US007829554B2

(12) United States Patent
Dobak (10) Patent No.: US 7,829,554 B2
(45) Date of Patent: Nov. 9, 2010

(54) SUSTAINED RELEASE ENHANCED LIPOLYTIC FORMULATION FOR REGIONAL ADIPOSE TISSUE TREATMENT

(75) Inventor: John D. Dobak, La Jolla, CA (US)

(73) Assignee: Lithera, Inc., San Diego, CA (US)

( * ) Notice: Subject to any disclaimer, the term of this patent is extended or adjusted under 35 U.S.C. 154(b) by 848 days.

(21) Appl. No.: 11/457,436

(22) Filed: Jul. 13, 2006

(65) Prior Publication Data

US 2007/0014843 A1      Jan. 18, 2007

Related U.S. Application Data

(60) Provisional application No. 60/699,155, filed on Jul. 14, 2005, provisional application No. 60/729,531, filed on Oct. 24, 2005, provisional application No. 60/732,981, filed on Nov. 3, 2005.

(51) Int. Cl.
| | |
|---|---|
| A01N 45/00 | (2006.01) |
| A01N 33/02 | (2006.01) |
| A01N 37/18 | (2006.01) |
| A61K 31/56 | (2006.01) |
| A61K 31/135 | (2006.01) |
| A61K 31/16 | (2006.01) |

(52) U.S. Cl. .................. 514/169; 514/651; 514/630; 514/171

(58) Field of Classification Search ................ 514/169, 514/651, 171, 630
See application file for complete search history.

(56) References Cited

U.S. PATENT DOCUMENTS

| | | | |
|---|---|---|---|
| 4,800,079 | A | 1/1989 | Boyer |
| 4,826,879 | A | 5/1989 | Yamamoto et al. |
| 5,126,147 | A | 6/1992 | Silvestri et al. |
| 5,314,916 | A | 5/1994 | York et al. |
| 5,496,803 | A * | 3/1996 | Meier et al. .................. 514/12 |
| 6,066,675 | A | 5/2000 | Wen et al. |
| 6,110,974 | A | 8/2000 | Aberg et al. |
| 6,656,508 | B2 | 12/2003 | Goldenberg et al. |
| 2002/0042404 | A1 | 4/2002 | Bauer et al. |
| 2003/0022856 | A1 | 1/2003 | Richardson et al. |
| 2004/0208910 | A1 | 10/2004 | Ashton et al. |
| 2005/0069591 | A1* | 3/2005 | Bernstein et al. ............ 424/489 |
| 2005/0113456 | A1* | 5/2005 | Aberg ........................ 514/649 |
| 2006/0189587 | A9 | 8/2006 | Bauer et al. |

FOREIGN PATENT DOCUMENTS

| | | |
|---|---|---|
| EP | 0120165 | 7/1990 |
| EP | 1153614 | 11/2001 |
| EP | 1867334 | 12/2007 |
| GB | 1471326 | 4/1977 |
| GB | 2443287 | 4/2008 |
| GB | 2453188 | 4/2009 |
| WO | WO 98/48810 | 11/1998 |
| WO | WO 01/28535 | * 10/1999 |
| WO | WO 01/19373 | 3/2001 |
| WO | WO 03/033000 | 4/2003 |
| WO | WO 2004/028545 | 4/2004 |
| WO | WO 2004/091574 | 10/2004 |
| WO | WO 2004/103057 | 12/2004 |
| WO | WO 2004/103379 | 12/2004 |
| WO | WO 2005/007145 | 1/2005 |
| WO | WO 2005/072745 | 8/2005 |
| WO | WO 2006/122165 | 11/2006 |
| WO | WO 2007/011743 | 1/2007 |

OTHER PUBLICATIONS

Johnson (Paediatric Respiratory Reviews, 2001, 2, 57-62).*
Fuller et al. (Respiratory Medicine, 1995, 89, A, 3-18).*
West, Anthony R., Solid State Chemistry and its Applications, Wiley, New York, 1988, pp. 358 & 365.*
Johnson, M., "The β-Adrenoceptor", Am J Respir Crit Care Med, 1998, vol. 158, No. 5, Nov. 1998, pp. S146-S153.
Reynisdottir, et al., "Effect of glucocorticosteroid treatment on β-adrenoceptor subtype function in adipocytes from patients with asthma," Clinical Science, Effect of glucocorticosteroid treatment on beta-adrenoceptor subtype function in adipocytes from patients with asthma, 1993, pp. 237-244, 85 Great Britain.
O E Brodde, et al., Terbutaline-induced desensitization of human lymphocyte beta 2-adrenoceptors. Accelerated restoration of beta-adrenoceptor responsiveness by prednisone and ketotifen, The Journal of Clinical Investigation, 1985, pp. 1096-1101, 76 PubMed Central.
Peter Arner, PhD, MD, "Human fat cell lipolysis: Biochemistry, regulation and clinical role," Best Practice & Research Clinical Endocrinology & Metabolism, 2005, pp. 471-482, vol. 19, Elsevier, Ltd.
EP 06787329.9 extended European search report dated Mar. 12, 2010.
GB 0718905.3 combined search and examination report dated Jan. 28, 2008.
GB 0718905.3 search report dated Nov. 27, 2008, claims 31-33.
GB 0718905.3 search report dated Nov. 27, 2008, claims 34-37 and 44.
GB 0718905.3 examination report dated Nov. 27, 2008.

(Continued)

*Primary Examiner*—Sreeni Padmanabhan
*Assistant Examiner*—Umamaheswari Ramachandran
(74) *Attorney, Agent, or Firm*—Wilson Sonsini Goodrich & Rosati (57) ABSTRACT

Compositions, formulations, methods, and systems for treating regional fat deposits comprise contacting a targeted fat deposit with a composition comprising long acting beta-2 adrenergic receptor agonist and a compound that reduces desensitization of the target tissue to the long acting beta-2 adrenergic receptor agonist, for example, glucocorticosteroids and/or ketotifen. Embodiments of the composition are administered, for example, by injection, and/or transdermally.

10 Claims, 1 Drawing Sheet

OTHER PUBLICATIONS

AU2006270165 examiner's first report dated Dec. 24, 2009.
GB 0804401.8 search report dated Apr. 15, 2009.
PCT/US2007/079740 search report mailed Jan. 30, 2008.
EP 07871172 supplementary European search report dated Mar. 1, 2010.
PCT/US2007/081568 search report mailed Jun. 17, 2008.
Adcock, "Molecular interactions between glucocorticoids and long-acting $\beta_2$-agonists," J Allergy Clin Immunol 110(6 Suppl):S261-8 (2002).
Bronnegard et al., "Effect of glucocorticosteroid treatment on glucocorticoid receptor expression in human adipocytes," J Clin Endocrinol Metab 80(12):3608-12 (1995).
Bujalska et al., "Characterisation of 11β-hydroxysteroid dehydrogenase 1 in human orbital adipose tissue: a comparison with subcutaneous and omental fat," J Endocrinol 192(2):279-88 (2007).
Caruso et al., "Topical fat reduction from the waist," Diabetes Obesity Metabolism 9:300-303 (2007).
Chung, "The complementary role of glucocorticosteroids and long-acting beta-adrenergic agonists," Allergy 53(42 Suppl):7-13 (1998).
De Mazancourt et al., "Correction by dexamethasone treatment of the altered lipolytic cascade induced by adrenalectomy in rat adipocytes," Horm Metab Res 22(1):22-4 (1990).
Farias-Silva et al., "Glucocorticoid receptor and Beta-adrenoceptor expression in epididymal adipose tissue from stressed rats," Ann NY Acad Sci 1018:328-32 (2004).
Fries, "Thyroid dysfunction: managing the ocular complications of Graves' disease," Geriatrics 47(2):58-60, 63-4, 70 (1992).
Gibaud et al., "Poly(ϵ-caprolactone) and Eudragit microparticles containing fludrocortisone acetate," Int J Pharm 28;269(2):491-508 (2004).
Gittoes and Franklyn, "Hyperthyroidism. Current treatment guidelines," Drugs 55(4):543-53 (1998).
Hadcock and Malbon, "Regulation of β-adrenergic receptors by "permissive" hormones: glucocorticoids increase steady-state levels of receptor mRNA," Proc Natl Acad Sci U S A 85(22):8415-9 (1988).
Kendall-Taylor et al., "Intravenous methylprednisolone in the treatment of Graves' ophthalmopathy," BMJ 297(6663):1574-8 (1988).
Lacasa et al., "Permissive action of glucocorticoids on catecholamine-induced lipolysis: direct "in vitro" effects on the fat cell beta-adrenoreceptor-coupled-adenylate cyclase system," Biochem Biophys Res Commun 153(2):489-97 (1988).
Langley et al., "Perioperative management of the thyrotoxic patient," Endocrinol Metab Clin North Am 32(2):519-34 (2003).
Mak et al., "Protective effects of a glucocorticoid on downregulation of pulmonary beta 2-adrenergic receptors in vivo," J Clin Invest 96(1):99-106 (1995).
Marcocci et al., "Orbital cobalt irradiation combined with retrobulbar or systemic corticosteroids for Graves' ophthalmopathy: a comparative study," Clin Endocrinol (Oxf) 27(1):33-42 (1987).
Mirkin, "Albuterol for weight control," www.DrMirkin.com (2009).
Page et al., "β-Adrenergic receptor agonists increase apoptosis of adipose tissue in mice," Domest Anim Endocrinol 26(1):23-31 (2004).
Pedersen et al., "Anti-glucocorticoid effects of progesterone in vivo on rat adipose tissue metabolism," Steroids 68:543-550 (2003).
Risse-Sundermann, "The treatment of alopecia areata by intradermal injections of microcrystallized prednisone trimethylacetate," Dtsch med Wochenschr 85(15):584-586 (1960).
Seco et al., "Acute and chronic treatment with glucocorticosteroids, modifying the beta 2-adrenergic response of the guinea pig trachea," Lung 173(5):321-8 (1995).
Wiersinga and Prummel, "Graves' ophthalmopathy: a rational approach to treatment," Trends Endocrinol Metab 13(7):280-7 (2002).
Dobak, "Formulations For Treatment Of Adipose Tissue, Cutaneous Tissue And Disorders, And Muscular Tissue," U.S. Appl. No. 12/445,571, filed Jan. 22, 2010.
Dobak, "Methods, Compositions, And Formulations For The Treatment Of Thyroid Eye Disease," U.S. Appl. No. 12/445,570, filed Jan. 12, 2010.
Reynisdottir, et al., "Effect of glucocorticosteroid treatment on β-adrenoceptor subtype function in adipocytes from patients with asthma," Clinical Science, Effect of glucocorticosteroid treatment on beta-adrenoceptor subtype function in adipocytes from patients with asthma, 1993, pp. 237-244, 85 Great Britain.
O E Brodde, et al., Terbutaline-induced desensitization of human lymphocyte beta 2-adrenoceptors. Accelerated restoration of beta-adrenoceptor responsiveness by prednisone and ketotifen, The Journal of Clinical Investigation, 1985, pp. 1096-1101, 76 PubMed Central.
Peter Arner, PhD, MD, "Human fat cell lipolysis: Biochemistry, regulation and clinical role," Best Practice & Research Clinical Endocrinology & Metabolism, 2005, pp. 471-482, vol. 19, Elsevier, Ltd.

* cited by examiner

FIG. 1

SUSTAINED RELEASE ENHANCED LIPOLYTIC FORMULATION FOR REGIONAL ADIPOSE TISSUE TREATMENT

CROSS-REFERENCE TO RELATED APPLICATIONS

This application claims the benefit under 35 U.S.C. §119 (e) of U.S. Provisional Application No. 60/699,155, filed Jul. 14, 2005; U.S. Provisional Application No. 60/729,531, filed Oct. 24, 2005; and of U.S. Provisional Application No. 60/732,981, filed Nov. 3, 2005, the entire contents of which are hereby incorporated by reference herein and made part of this specification.

BACKGROUND OF THE INVENTION

1. Field of the Invention

This disclosure relates generally to medical treatment, and more particularly to the treatment of fat deposits.

2. Description of the Related Art

Adipose tissue is the primary energy storage tissue of the body. Fat cells, or adipocytes, store this energy in the form of triglycerides. Triglycerides are mobilized from fat stores to provide caloric energy to the body through hormonal induction of triglyceride hydrolysis. This process releases free or non-esterified fatty acids and glycerol into the blood for use by other body tissues. The breakdown of triglycerides from fat store is referred to as lipolysis. Growth of new adipocytes also occurs, which is referred to as adipogenesis.

Weight loss programs involving exercise can stimulate lipolysis through adrenergic stimulation resulting in fat reduction. Primary hormones and neurotransmitters that control lipolysis in the body are the catecholamines. Adipose tissue has beta-1, 2, and 3 adrenergic receptors and alpha-2 adrenergic receptors. Binding of beta agonists to beta receptors in adipose tissue can result in adipocyte lipolysis, while binding of alpha receptor agonists can inhibit lipolysis. Beta receptor activation can also inhibit adipogenesis. In humans, the beta-2 receptor are often the most abundant on fat cell surfaces and the primary mediator of beta receptor-stimulated lipolysis. Stimulation of lipolysis by beta agonists is mediated by adenylate cyclase and increased formation of cyclic adenosine monophosphate (cyclic AMP, cAMP).

Accumulation of fat stores can occur unevenly in the body. For example, persons may accumulate fat predominantly in the abdominal cavity while others predominately in the subcutaneous tissue. Gender differences may also be apparent with women accumulating fat in the thighs and lateral buttocks and males in the waist. Women may accumulate fatty deposits of the thighs, which have a rumpled or "peau-de-orange" appearance, resulting in a condition referred to as cellulite. Cellulite may be related to skin architecture which allows subdermal fat herniation, sometimes referred to as adipose papillae. Other factors that may be related to cellulite include altered and/or reduced connective tissue septae, vascular and lymph changes that lead to fluid accumulation, and inflammation. Fat tissue may also accumulate in the form of a fibrous fatty deposit known as a lipoma.

Similarly, utilization of fat stores may occur unevenly. Persons who have lost substantial weight may still have regional pockets of fat accumulation that are resistant to reduction unless unhealthy extremes of weight loss are achieved. Exercise may affect subcutaneous fat stores differently, with deeper tissues responding with lipolysis and superficial stores being more resistant. Cellulite may also still be present despite weight loss, and lipomas are typically not affected by weight loss.

Differential utilization of fat stores may be in part due to the action of adrenergic receptors. Thus, certain regions may have higher alpha-2 receptor activity or a higher number of alpha-2 receptors relative to beta-2 receptors, leading to a reduction of lipolysis. Studies have shown a difference in lipolytic activity in response to beta adrenergic receptor stimulation in adipose tissue of the omentum versus the subcutaneous abdomen versus the thigh, with the omentum having the highest activity and the thigh having the lowest activity. The differences in lipolytic activity can be abolished by the addition of an alpha-2 receptor antagonist, suggesting that excessive alpha-2 receptor activities is a cause for lower lipolytic response to adrenergic stimulation in different adipose tissue regions.

Delivery of adrenergic active ingredients into the subcutaneous tissue, both beta agonists and alpha-2 antagonists, has been proposed and has been shown to result in regional fat loss and improved appearance of regional fat accumulations. For example, isoproterenol 11 and yohimbine 8 have been shown to reduce the thigh circumference in women. These studies required subcutaneous injections of beta agonists three to five times per week in multiple locations over the thighs. This is not practical as a commercially viable product for regional fat loss and would cause significant discomfort to the patient. Because these lipolytic agents, especially the beta agonists, are short-acting and may be rapidly removed from the adipose tissue, the lipolysis is likely to have occurred for only a short time after the injection thereby reducing the potential magnitude of the effect despite the multiple injections. Additionally, long term exposure of adipocytes to beta agonists results in receptor desensitization and down regulation, and a loss of lipolytic activity. Means to reduce or prevent these effects on the receptor may also improve the therapy.

SUMMARY OF THE INVENTION

Compositions, formulations, methods, and systems for treating regional fat deposits comprise contacting a targeted fat deposit with a composition comprising long acting beta-2 adrenergic receptor agonist and a compound that reduces desensitization of the target tissue to the long acting beta-2 adrenergic receptor agonist, for example, glucocorticosteroids and/or ketotifen. Embodiments of the composition are administered, for example, by injection, and/or transdermally.

Some embodiments provide an injectable formulation for adipose tissue accumulation comprising: a long acting selective beta-2 adrenergic receptor agonist; a compound for reducing desensitization of adipose tissue to a beta-adrenergic receptor agonist; and a liquid carrier.

In some embodiments, the long acting selective beta-2 adrenergic receptor agonist is lipophilic. In some embodiments, the long acting selective beta-2 adrenergic receptor agonist comprises at least one of salmeterol, formoterol, salts thereof, and solvates thereof.

In some embodiments, the compound for reducing desensitization of the target tissue to a beta-adrenergic receptor agonist comprises a glucocorticosteroid. In some embodiments, the compound for reducing desensitization of the target tissue to a beta-adrenergic receptor agonist comprises an antihistamine. In some embodiments, the compound for reducing desensitization of the target tissue to a beta-adrenergic receptor agonist comprises a glucocorticosteroid and an antihistamine. In some embodiments, the compound for reducing desensitization of the target tissue to a beta-adrenergic receptor agonist comprises at least one of dexamethasone, prednisolone, fluticasone proprionate, budesonide, ketotifen, and analogs thereof.

In some embodiments, the liquid carrier comprises a lipophilic liquid carrier.

In some embodiments, at least one of the long acting selective beta-2 adrenergic receptor agonist and the compound for reducing desensitization is loaded on a sustained release agent. In some embodiments, the sustained release agent comprises at least one of a biodegradable polymer, a biodegradable copolymer, a hydrogel, and a liposome. In some embodiments, the sustained release agent comprises poly (lactide glycolide). In some embodiments, an active ingredient loading on the poly(lactide glycolide) is up to about 75%.

Some embodiments comprise at least one of salmeterol, a salt thereof, and a solvate thereof; and fluticasone.

Some embodiments comprise at least one of formoterol, a salt thereof, and a solvate thereof; and budesonide. Some embodiments comprise at least one of salmeterol, formoterol, salts thereof, and solvates thereof; and ketotifen.

Other embodiments provide an injectable formulation for treating fat accumulation comprising: at least one long acting selective beta-2 adrenergic receptor agonist; a means for reducing desensitization of the target tissue to a beta-adrenergic receptor agonist; and a liquid carrier. In some embodiments, the at least one long acting selective beta-2 adrenergic receptor agonist comprises at least one of salmeterol, formoterol, salts thereof, and solvates thereof.

Other embodiments provide a method for treating a fat accumulation comprising: contacting a fat accumulation with a pharmaceutically effective amount of a long acting selective beta-2 adrenergic receptor agonist; and contacting a fat accumulation with a pharmaceutically effective amount of a compound for reducing desensitization of the target tissue to a beta-adrenergic receptor agonist.

In some embodiments, the long acting selective beta-2 adrenergic receptor agonist comprises at least one of salmeterol, formoterol, salts thereof, and solvates thereof.

In some embodiments, the compound for reducing desensitization of the target tissue to a beta-adrenergic receptor agonist comprises at least one of a glucocorticosteroid, dexamethasone, prednisolone, fluticasone proprionate, budesonide, and ketotifen.

In some embodiments, at least one of the long acting selective beta-2 adrenergic receptor agonist and the compound for reducing desensitization is loaded on a sustained release agent.

In some embodiments, the long acting selective beta-2 agonist comprises salmeterol and the pharmaceutically effective amount of salmeterol is up to about 100 µg/day. In some embodiments, the long acting selective beta-2 agonist comprises formoterol and the pharmaceutically effective amount of formoterol is up to about 50 µg/day.

In some embodiments, the long acting selective beta-2 adrenergic receptor agonist and the compound for reducing desensitization are delivered substantially simultaneously. In some embodiments, at least one of the long acting selective beta-2 adrenergic receptor agonist and the compound for reducing desensitization is delivered by single needle injection. In some embodiments, at least one of the long acting selective beta-2 adrenergic receptor agonist and the compound for reducing desensitization is delivered by needleless injection. In some embodiments, at least one of the long acting selective beta-2 adrenergic receptor agonist and the compound for reducing desensitization is delivered transdermally.

Other embodiments provide a method for reducing adipose tissue comprising: administering a pharmaceutically effective amount of a compound, wherein the compound increases beta-2 adrenergic receptors in a region of adipose tissue; and administering a pharmaceutically effective amount of a selective long acting beta-2 receptor agonist to the region of adipose tissue, thereby resulting in the region of adipose tissue exhibiting at least one of lipolysis and inhibited adipogenesis.

In some embodiments, at least one of the administering the compound and the administering the beta-2 receptor agonist is performed less frequently than once per day.

Other embodiments provide a method for treating regional fat accumulations or cellulite comprising: administering to a regional fat accumulation or cellulite a composition comprising: a long acting selective beta-2 agonist; and at least one of a glucocorticosteroid and ketotifen, wherein the composition exhibits sustained lipolytic activity thereby promoting lipolysis in the regional fat accumulation or cellulite.

In some embodiments, the long acting selective beta-2 agonist comprises at least one of salmeterol, formoterol, salts thereof, and solvates thereof.

Some embodiments provide a controlled release formulation comprising a controlled release carrier, a long acting selective beta-2 adrenergic receptor agonist, and a glucocorticosteroid. The controlled release carrier reduces fat in the treatment of regional fat accumulation. In some embodiments, the long acting selective beta-2 agonist is salmeterol and/or formoterol. In some embodiments, the controlled release carrier is a biodegradable polymer. In some embodiments, the biodegradable polymer is comprises lactide and glycolide. In some embodiments, the biodegradable polymer is formulated as a microparticle. In some embodiments, the glucocorticoid is fluticasone, budesonide, and/or dexamethasone. In some embodiments, at least a portion of the formulation is delivered to the fat accumulation through a needleless injection device. In additional embodiments, the needleless injection device promotes the lateral spread of the formulation in the fat accumulation.

Some embodiments provide a method for reducing adipose tissue by treating a region of fat involves the administration of pharmacologically effective amounts of a glucocorticosteroid or ketotifen to a region of fat. The glucocorticosteroid or ketotifen increases the beta-2 adrenergic receptors on the adipocytes in the fat region, thereby improving the lipolytic activity and/or adipogenesis inhibition of a co-administered selective long acting beta-2 receptor agonist to the regional fat accumulation.

In some embodiments, the long acting selective beta-2 agonist is salmeterol. In some embodiments, the pharmacologically effective amount of salmeterol is up to about 100 micrograms per day. In some embodiments, the long acting selective beta-2 agonist is formoterol In some embodiments, the pharmacologically effective amount of formoterol is up to about 50 micrograms per day.

Some embodiments provide a method for treating a region of fat comprising administering a pharmacologically effective formulation comprising a lipophilic, substantially selective beta-2 receptor agonist with sustained adrenergic activity in adipose tissue, thereby causing sustained lipolysis. Some embodiments of the method further comprise co-administering a glucocorticosteroid or ketotifen to further sustain and enhance lipolysis. Some embodiments of the method further comprise administering the formulation less than once each day.

Some embodiments provide a method for treating regional fat accumulations or cellulite comprising administering a composition comprising a long acting substantially selective beta-2 agonist, and a glucocorticosteroid or ketotifen. Embodiments of the method promote lipolysis in resistant fat tissue and exhibit sustained lipolytic activity, thereby reducing regional fat accumulation and improving the appearance of cellulite.

DETAILED DESCRIPTION OF THE PREFERRED EMBODIMENT

Figure 1:
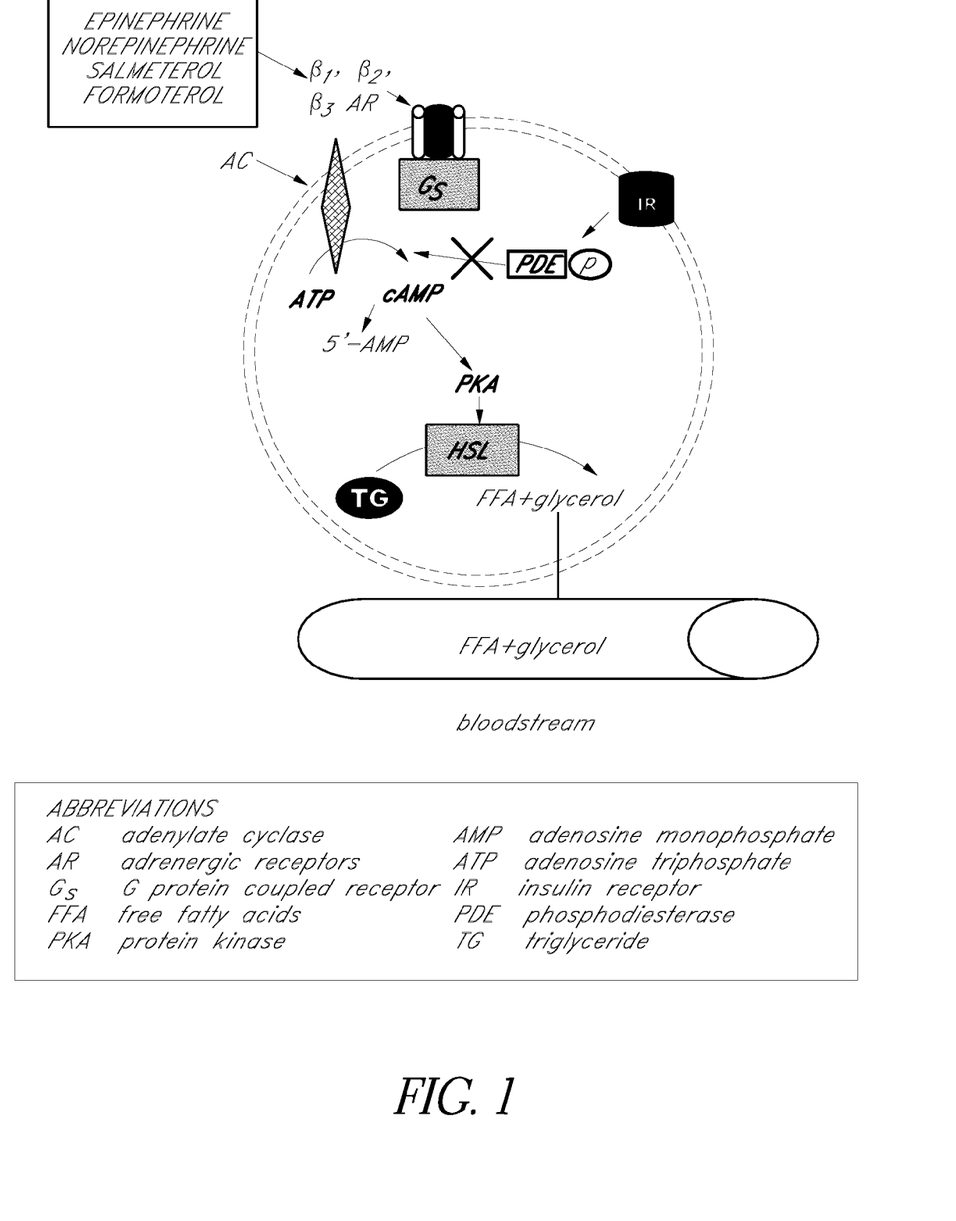
FIG. 1 schematically illustrates adipocyte lipolysis.

Embodiments of pharmaceutical compositions, formulations, methods, and systems achieve regional fat, adipose tissue, and adipocyte reduction therapy through adrenergic system modulation. As used and/or cited herein, the term "modulation" is generally used in its usual sense, and more particularly to refer to adrenergic receptor agonism, adrenergic receptor antagonism, and/or changes in receptor signaling pathways. One example of a change in receptor signaling pathways includes an increase in cyclic AMP, for example as illustrated schematically in FIG. 1. In some embodiments, modulation refers to receptor upregulation or an increase in the number of adrenergic receptors, a decrease in receptor deactivation or sequestration, receptor activity changes (for example, an increase in activity), and/or changes in receptor affinity.

It is believed that some embodiments of sustained modulation of adrenergic receptors in adipose tissue result in some combination of sustained lipolysis, reduced lipid content of the adipocyte, reduced adipocyte cell size, reduced adipose tissue mass or fat accumulation, and/or improved cosmetic appearance. Some embodiments provide selective reduction of regional and/or subcutaneous accumulations of adipose tissue and adipocytes, including cellulite, through sustained adrenergic modulation. Sustained adrenergic modulation result in sustained inhibition of fat cell proliferation (adipogenesis) in some embodiments. In some embodiments, the composition is useful for treating cellulitic fat accumulation and/or lipomas.

Embodiments of the disclosed pharmaceutical compositions comprise one or more long acting selective beta-2 adrenergic receptor agonists in combination with one or more compounds that reduce desensitization of the target tissue to the beta-adrenergic receptor agonist(s), for example, glucocorticosteroids or ketotifen, or analogs thereof. The term desensitization includes both short term desensitization (tachyphylaxis), as well as long term desensitization, as well as desensitization over other time periods. Beta-2 adrenergic receptor agonists are also referred to herein as "beta-2 agonists" and "beta-2 receptor agonists." Unless otherwise specified, references to beta-2 adrenergic receptor agonists also include their analogs, physiologically acceptable salts and/or solvates known in the art. Some embodiments of the composition comprise from about 100:1 to about 1:100 long-acting selective beta-2 agonist to glucocorticosteroid.

As discussed above, lipolytic activity and adipocyte proliferation inhibition are believed to be mediated through modulation of adrenergic receptors in adipose tissue and/or on adipocytes. In some embodiments, the reduction therapy is enhanced through prolonged exposure or sustained activity of one or more adrenergic receptor agonists and/or receptor pathway stimulating compounds known in the art, for example, catecholamines, beta agonists, alpha antagonists, forskolin, aminophylline, analogs thereof, or combinations thereof.

Some embodiments provide sustained adrenergic modulation through the use of pharmaceutical compositions comprising one or more long-acting substantially selective beta-2 receptor agonists. Some embodiments of the sustained activity pharmaceutical composition comprise one or more suitable long-acting, selective beta-2 agonists known in the art, for example, salmeterol 1, formoterol 2, bambuterol 3, physiologically acceptable salts or solvates thereof, or combinations thereof.

Sustained adrenergic modulation is not observed in the subcutaneous delivery of typical adrenergic compositions because the adrenergic compound is generally rapidly removed from the adipose tissue through the blood and/or lymph. Furthermore, long-term exposure of adipose tissue to adrenergic agents, particularly beta receptor agonists, is believed to result in receptor desensitization through receptor phosphorylation and sequestration. It is believed that these effects limit the ability of an adrenergic modulating composition to treat adipose tissue and result in tachyphylaxis, a condition in which the body experiences a rapidly decreasing response to the agonist following administration of the initial doses, to the desired lipolytic and anti-adipogenesis effect. Consequently, the treatment effect is short lived and frequent dosing is required.

Short-acting beta-2 agonists often result in tachyphylaxis, as discussed above. However, because preferred embodiments of long-acting selective beta-2 agonists have substantially selective beta-2 receptor activity and high lipophilicity, the activities of long-acting beta-2 agonists continue for longer periods of time in adipose tissue compared with short-acting beta-2 agonists. Partial beta-2 receptor antagonist activity prevents desensitization that can occur with continuous exposure of adipocytes to full adrenergic agonists. Consequently, long-acting selective beta-2 agonists exhibit a reduced tachyphylaxis. Compared with short-acting beta-2 agonists, lipolysis also occurs for a longer time after administration because long-acting selective beta-2 agonists have longer half-lives. The combination of longer half-lives and activities reduces the frequency of administration of the pharmaceutical compositions. Consequently, in some embodiments, daily administration of the composition is not required. Moreover, preferred embodiments of long-acting selective beta-2 agonists also exhibit greater selectivity for beta-2 receptors, permitting substantially similar therapeutic effects compound with short-acting beta-2 agonists at a lower dosage.

As discussed above, lipolysis and/or inhibition of adipogenesis are stimulated by the beta-1, 2, or 3 receptor subtypes. Thus, agonists to one, two and/or all three receptors are capable of stimulating lipolysis and/or inhibition of adipogenesis. In humans, beta-2 receptor activity is believed to be more important for stimulating lipolysis, particularly in the presence of an anti-inflammatory steroid or glucocorticosteroid.

Long-acting selective beta-2 agonists, for example, salmeterol 1 (±2-(hydroxymethyl)-4-[1-hydroxy-2-[6-(4-phenylbutoxy)hexylamino]ethyl]-phenol, CAS Reg. No. 94749-08-3), and formoterol 2 (±N-[2-hydroxy-5-[1-hydroxy-2-[1-(4-methoxyphenyl)propan-2-ylamino]ethyl]-phenyl] methanamide, CAS Reg. No. 73573-87-2), are preferred in some embodiments. Some embodiments of the compositions comprise one or more long-acting selective beta-2 agonists as physiologically acceptable salts or solvates known in the art, for example, salmeterol xinafoate and/or formoterol fumarate. Those skilled in the art will understand that in many cases, salts and/or solvates of a beta-2 agonists will have the desired activity. Accordingly, unless otherwise specified, references to an active ingredient, for example, to salmeterol 1, formoterol 2, isoproterenol 4, albuterol 5, fenoterol, and forskolin, include the compounds themselves as well as a physiologically acceptable analogs, salts, and/or solvates thereof, or combinations thereof.

Some preferred long-acting beta agonists exhibit high intrinsic adenylate cyclase activity, which increase cAMP synthesis. For example, some embodiments comprise formoterol 2 as a long-acting beta-2 selective agonist, which exhibits some combination of higher potency, reduced systemic effects, high intrinsic activation of adenylate cyclase, and/or increases in cyclic AMP, a mediator of lipolysis.

In some preferred embodiments formoterol 2 is present as a physiologically acceptable salt and/or solvate thereof. Suitable physiologically acceptable salts of formoterol 2 are known in the art, for example, acid addition salts derived from inorganic and organic acids, such as the hydrochloride, hydrobromide, sulfate, phosphate, maleate, fumarate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate succinate, lactate, glutarate, gluconate, tricarballylate, hydroxynaphthalenecarboxylate, oleate, combinations thereof, and the like. Preferred embodiments comprise formoterol 2 as its fumarate salt and/or as a dihydrate. Suitable tissue concentration of formoterol 2 for adipose tissue treatment include from about 1 pM to about 100 µM, more preferably from about 10 pM to about 100 nM.

Some preferred embodiments comprise salmeterol 1 as a long-acting beta-2 agonist. Salmeterol 1 exhibits partial agonist activity, which is believed to reduce receptor desensitization. In some preferred embodiments salmeterol 1 is present as a physiologically acceptable salt and/or solvate thereof. Suitable physiologically acceptable salts of salmeterol 1 are known in the art, for example acid addition salts derived from inorganic and organic acids, such as the hydrochloride, hydrobromide, sulfate, phosphate, maleate, tartrate, citrate, benzoate, 4-methoxybenzoate, 2-hydroxybenzoate, 4-hydroxybenzoate, 4-chlorobenzoate, p-toluenesulphonate, methanesulphonate, ascorbate, salicylate, acetate, fumarate, succinate, lactate, glutarate, gluconate, tricarballylate, hydroxynaphthalenecarboxylate, 1-hydroxy-2-naphthalenecarboxylate, 3-hydroxy-2-naphthalenecarboxylate, oleate, combinations thereof, and the like. Some preferred embodiments comprise salmeterol 1 as the 1-hydroxy-2-naphthalene carboxylate salt (hydroxynaphthoate). Suitable tissue concentration of salmeterol 1 for adipose tissue treatment ranges from about 1 pM to about 100 µM, preferably from about 10 nM to about 10 µM.

Some embodiments comprise optically pure isomers of the beta adrenergic agonist(s), which improve lipolysis and adipogenesis inhibition and reduce potential side effects. In some embodiments, these optically pure isomers allow formulations comprising larger loadings of an active ingredient, for example, by eliminating one or more isomers with no physiological effect, a lesser a physiological effect, a negative effect, and/or an undermined physiological effect. Removing the undesired bounds of a racemic mixture isolates the active isomer, or eutomer, thereby allowing more eutomer to be loaded in a give formulation by removing the inactive components.

Two stereogenic centers in a molecule generally generate two diastereomers, referred to herein as (R*,R*) and (R*,S*), and their enantiomers. Diastereomers are stereoisomers that are not enantiomers, that is, the mirror image of one diastereomer is not superimposable on another diastereomer. Enantiomers are stereoisomers that are mirror images of each other. A racemate is a 1:1 mixture of enantiomers. The enantiomers of the (R*,R*) diastereomers are referred to as the (R,R) and (S,S) enantiomers, which are mirror images of each other and therefore share some chemical and physical properties, for example melting points. Similarly, the (R,S) and (S,R) isomers are enantiomers of the (R*,S*) enantiomer. For example, formoterol 2 is available as a racemate of the (R,R)- and (S,S)-isomers in a 1:1 ratio, typically as the dihydrate of the fumarate salt. Some preferred embodiments comprise the (R,R) enantiomer, (R,R)-formoterol, which is more active as a long-acting beta-2 agonist. Some embodiments comprise optically pure isomers of other beta-2 agonists, for example, (R)-salmeterol.

Additionally, in some embodiments of the pharmaceutical composition, at least one long-acting selective beta-2 agonists is highly lipophilic, thereby providing a pharmaceutical composition with sustained activity in fat tissue. It is believed that high lipid solubility extends the residence time of the beta-2 agonist in the adipose tissue, thereby eliminating or reducing the need for a sustained release and/or controlled release carrier in some embodiments. Elimination of a sustained release and/or controlled release carrier provides some combination of simplified formulation, reduced cost, and/or improved safety. In formulations comprising a sustained release carrier, for example, a sustained release polymer, the highly lipophilic of the beta-2 agonist facilitates incorporation into the sustained release carrier, as discussed in greater detail below.

Salmeterol 1 and formoterol 2 have high lipid solubilities, which extends the residence time in the adipose tissue and/or in one or more adipose cells. Some embodiments of the composition comprise a highly lipophilic beta agonist, which reduces or eliminates the need for a sustained or controlled release carrier due to partitioning and sequestration in the adipose tissue thereby prolonging the treatment effect. In some embodiments, beta agonists with an oil-water partition coefficient of at least about 1000 or at least about 10,000 to 1 are preferred. For example, salmeterol 1 is at least 10,000 times more lipophilic than albuterol 5, a short acting hydrophilic beta agonist. Additionally, salmeterol 1 and formoterol 2 have anti-inflammatory properties, used in the treatment of cellulite as discussed below. In some embodiments, they also promote favorable extracellular matrix changes and reduce fluid accumulation, which improves the treatment of cellulite and regional fat accumulation.

Sustained activity is further enhanced by preventing desensitization (tachyphylaxis) that can occur with continuous exposure of adipocytes to adrenergic agonists as discussed above. Compounds that reduce desensitization of the target tissue to the beta-adrenergic receptor agonists are referred to generically as "glucocorticosteroids," although the term encompasses all suitable compounds that reduce tolerance of the target tissue to the beta-adrenergic receptor agonists, including glucocorticosteroids and suitable antihistimines, for example, ketotifen. Glucocorticosteroids are also referred herein as "anti-inflammatory steroids," "glucocorticoids," and/or "corticosteroids." Glucocorticoids are believed to sensitize resistant fat accumulations by increasing the number of beta-2 receptors, thereby favoring lipolysis or fat reduction over fat storage. Glucocorticoids are also believed to decrease the number of alpha-2 receptors. Estrogen can induce the expression of alpha-2 adrenergic receptors in subcutaneous adipose tissue in women resulting in a ratio of beta-2 receptor to alpha-2 receptor of less than 1. A ratio of beta-2 receptors to alpha-2 receptors greater than about 1 is believed to cause fat reduction rather than fat accumulation in adipocytes. Some embodiments of the composition comprising one or more glucocorticosteroids are effective in treating regions of fat comprising a reduced number of beta-2 receptors and or an increased number of alpha-2 receptors, which are resistant to beta adrenergic stimulation of lipolysis or inhibition of adipogenesis, for example, subcutaneous adipose tissue, especially women.

The glucocorticosteroid is believed to improve lipolysis, adipogenesis inhibition, and/or regional fat reduction during beta agonist exposure. In some embodiments, treatment of adipocytes with a glucocorticosteroid that increases lipolytic activity maintains and/or increases both lipolytic activity and the number of beta-receptors in the target tissue. Examples of suitable corticosteroids include dexamethasone 6, prednisolone, fluticasone proprionate 7, budesonide 8, and their analogs. In some preferred embodiments, the glucocorticoid is dexamethasone 6 (9-fluoro-11,17-dihydroxy-17-(2-hydroxyacetyl)-10,13,16-trimethyl-6,7,8,11,12,14,15,16-octahydrocyclopenta[a]phenanthren-3-one, CAS Reg. No. 50-02-2) and/or fluticasone proprionate 7. As discussed above, another preferred compound for reduce desensitization is ketotifen 9, which is also useful as an antihistamine. Some embodiments of the composition comprise one compound that reduces desensitization of the adipose tissue to the beta-2 agonist. Other embodiments comprise a plurality of desensitizing compounds, for example, a plurality of glucocorticosteroids. Some preferred embodiments comprise at least one glucocorticosteroids and the antihistamine ketotifen. It is believed that the combination of glucocorticosteroid and ketotifen is more effective at reducing desensitization because ketotifen prevents beta receptor sequestration, while the glucocorticosteroid increases the beta-receptor number, thereby synergistically potentiating the overall effect on the beta receptor. Analogs of ketotifen are also suitable.

-continued

8

9 tic rate than visceral fat. Exposing subcutaneous fat to anti-lipolytic blocking agents improves lipolytic activity in some embodiments.

10

11

Some embodiments of the composition comprise other adrenergic agents that enhance the effect of the long-acting selective beta-2 agonist. For example, aminophylline 12 (1,3-dimethyl-7H-purine-2,6-dione, diethylamine CAS Reg. No. 317-34-0) and theophylline 13 (CAS Reg. No. 58-55-9) are lipolytic agent that block the breakdown of cyclic AMP.

12

13

In some embodiments, at least one of beta-2 receptor activity or density increases in human subcutaneous adipocytes in response to the anti-inflammatory steroid or ketotifen administration, particularly in the presence of a beta agonist. In some embodiments, increasing beta-2 receptor activity and/or density potentiates the effect of long- and short-acting beta-2 agonists. Additionally, in some embodiments, it is believed that glucocorticosteroid exposure downregulates anti-lipolytic alpha-2 adrenergic receptors, which is particularly beneficial, for example, in subcutaneous fat, which often has a high number of these receptors. Thus, in some embodiments, the glucocorticosteroid sensitizes subcutaneous fat to the effects of beta-2 receptor stimulation, lipolysis, inhibition of adipogenesis, and/or apoptosis, and/or increases the ratio of beta-2 adrenergic receptors to alpha-2 adrenergic receptors, thereby shifting the balance of the adipose tissue from fat accumulation to fat loss.

Some embodiments of the composition comprise additional optional ingredients. For example, certain fat accumulations such as cellulite and lipomas comprise fibrous connective tissue. In some situations, it is advantageous to degrade this fibrous connective tissue, for example, to improve the appearance of the overlying skin. Some embodiments of the composition comprise an enzyme such as collagenase, which degrades the collagen in the fibrous connective tissue.

Some embodiments of the composition comprise one or more anti-lipolytic blocking agents known in the art, for example, selective alpha-2 receptor antagonists such as phentolamine 10 (CAS Reg. No. 73-05-2) or yohimbine 11 (CAS Reg. No. 146-48-5) block anti-lipolytic effects in regional fat accumulation. Anti-lipolytic effects in adipocytes and adipose tissue are typically observed in subcutaneous and regional areas of fat accumulation. For example, when exposed to beta agonists, subcutaneous fat has a lower lipoly- Other optional ingredients increase the secondary signals created by the beta agonist binding. For example, in some embodiments, some embodiments, the composition comprises forskolin 14 (CAS Reg. No. 66575-29-9), which stimulates adelylate cyclase, thereby increasing the synthesis of cyclic AMP initiated by the long-acting beta agonist. The increased concentration of cyclic AMP helps sustain lipolytic activity.

14

Some embodiments of the composition comprise growth hormone in combination with a long-acting beta agonist and glucocorticosteroid, which appears to stimulate lipolysis.

Others embodiments of the composition further comprises one or more nonselective beta agonists, for example, isoproterenol 4, and/or short-acting selective beta-2 agonists, for example, terbutaline. Some compositions comprise at least one of an alpha-2 antagonist, or physiologically acceptable salts or solvates thereof.

Embodiments of the composition are formulated for administered by any suitable method known in the art, for example, as described in *Remington: The Science And Practice Of Pharmacy* (21st ed., Lippincott Williams & Wilkins). In some embodiments, the composition is formulated for injection of an area at which treatment is desired, for example, at a subcutaneous fat deposit.

Suitable excipients for injectable formulations are known in the art. In some embodiments, one or more of the beta-2 receptor agonists or glucocorticosteroids are formulated in a liquid carrier, for example, as a solution, a suspension, a gel, and/or an emulsion. Some embodiments comprise any suitable lipophilic excipient known in the art, for example, modified oils (e.g., Cremophor® BASF), soybean oil, propylene glycol, polyethylene glycol, derivatized polyethers, combinations thereof, and the like. Some embodiments comprise a microparticulate and/or nanoparticulate carrier for at least one of the beta-2 receptor agonists and/or glucocorticosteroids, as discussed in greater detail below. Some embodiments comprise one or more sustained or controlled release carriers or agents, for example, polymer microspheres.

Injectable formulations are administered using any mean known in the art, for example, using a single needle, multiple needles, and/or using a needleless injection device. In some embodiments, a tissue loading dose of the active ingredients formulated in a suitable carrier delivered by injection. In some embodiments, delivery comprises single needle injection. In some embodiments, delivery comprises injection using a multi-needle array, which, in some embodiments, provides a wide dispersion of the formulation in the target tissue. In some embodiments, formulations are injected in a manner that allows dispersal into the appropriate layer of subcutaneous fat in areas where regional fat reduction is desired, such as the submental region, the waist/hip, the lateral buttocks or thigh, or the periorbital fat regions. In some embodiments, the formulation is injected in aliquots of from about 0.5 mL to about 1.0 mL. In some embodiments, aliquots of the formulation are injected over an area of from about 10 cm$^2$ to about 20 cm$^2$.

Another delivery mode comprises a needleless pressurized injection device. In some embodiments, of these devices, the formulation is pressurized mechanically or pneumatically, for example, using a gas such as helium or carbon dioxide, and then forced through a small orifice into the body tissues, thereby delivering the formulation subcutaneously. Suitable formulations for needleless injection are known in the art, for example, liquid, solutions, suspensions, gels, colloids, emulsions, and dry powders. An advantage of this system is a wide dispersal area compared with typical needle injection systems. Needleless injection under the appropriate pressure forces the formulation into a more planar delivery pattern, with fingers of formulation spreading out radially following paths of least resistance. In contrast, delivery by a typical needle injection results in a globular delivery of the formulation. Needleless injection also permits precise control of the depth of penetration by controlling the injection pressure and orifice size. Thus, needleless injection is a preferred delivery method for a sub-dermal injection of a formulation for treating superficial fat accumulations, which is useful, for example, for smoothing skin dimpling caused by fat. In some embodiments, needleless injection is also used for deeper, sub-dermal sub-fascial injections targeting deeper fat accumulations. A needleless device also provides easy and convenient multiple injections of the formulation over a defined region with a large lateral spread.

In some embodiments, the beta-2 agonist and compound that reduces desensitization are administerd separately, for example, injected as separate formulations. Co-administration of a beta-2 agonist with a compound that reduces desensitization is preferred in some embodiments, however, because the reduced desensitization is observed only in the presence of the beta-2 in some cases.

Some embodiments of the formulation comprise one or more sustained or controlled release agents known in the art for providing a sustained or controlled release of a beta-2 agonist and/or glucocorticosteroid, which are, for example, encapsulated in, bound to, and/or conjugated to the sustained or controlled release agent or carrier. In some embodiments, biocompatible, biodegradable sustained or controlled release formulations provide local tissue activity for weeks to months. Suitable sustained or controlled release agents or carriers are known in the art, for example, polymers, macromolecules, active ingredient conjugates, hydrogels, contaminations thereof, and the like. Some embodiments of the sustained release carrier target fat, for example, liposomes. Preferably, the sustained release materials are selected to facilitate delivery of a substantially equal amount of the active substance per unit time, particularly over the course of at least about 3 days, more particularly at least about 4 days, to up to one year or greater. Several rounds of injections of the sustained release formulation can be made over time to treat a single area.

In some embodiments, the sustained release agent comprises a polymer, for example, polylactides, polyglycolides, poly(lactide glycolides) polylactic acids, polyglycolic acids, polyanhydrides, polyorthoesters, polyetheresters, polycaprolactones, polyesteramides, polycarbonates, polycyanoacrylates, polyurethanes, polyacrylates, and blends, mixtures, or copolymers of the above, which are used to encapsulate, binds, or conjugate with the active ingredients(s) (e.g., beta agonists and/or glucocorticosteroids). Some preferred embodiments of sustained release polymers comprise polyethylene glycol groups to which one or more of the active ingredients is conjugated. In some preferred embodiments, the sustained release agent comprises poly(lactide glycolide) (PLGA, poly(lactic-co-glycolic acid)) copolymer 15.

Some embodiments of the sustained release agent comprise one or more hydrogels known in the art, for example, modified alginates. Examples of suitable modified alginates include those disclosed in WO 98/12228. Some embodiments of the sustained release agent comprise an albumin-based nano-particle carrier or excipient.

In some embodiments, a formulation comprising a prepolymer solution is injected into the target tissue site, where it is then polymerized (e.g., by photopolymerization) or solidified (e.g., by using temperature sensitive gelling materials) in vivo.

In some embodiments, the controlled release materials here release characteristics designed for the particular application of tissue reduction. In some embodiments, the sustained release or controlled release agent is formed into microparticles, such as microspheres, which are formulated as an injectable solution and/or gel. In some embodiments, the microparticles are from about 10 µm to about 100 µm in diameter and generally uniform in size. For example, in some embodiments, formulations comprising alginates and/or poly (lactide-co-glycolide)s 15 are provided as an injectable gel or processed into microspheres using methods known in the art. Other examples of suitable injectable biodegradable, biocompatible materials suitable for microparticle formation include chitosan, dextran, hydroxyapetite, and silicon.

Microspheres and/or microparticles are formed using any method known in the art, for example, by a solvent evaporation and/or emulsion polymerization. In some embodiments, the microspheres have average diameters of from about 5 µm to about 60 µm, preferably, about 20 µm. In some embodiments, PLGA is manufactured with varying ratios of lactide to glycolide depending on the desired rate of release of the active ingredient(s). Because the rate of degradation of this copolymer is proportional to its crystallinity and the proportion of glycolide in the formulation, non-racemic mixtures of the lactide and/or glycolide increase crystallinity and slow the rate of degradation. Higher proportions of glycolide increase the rate of degradation. In some embodiments, a ratio of about 65%-75% lactide to about 25%-35% glycolide provides active ingredients released over from about 2 weeks to about 45 days. In other embodiments, the ratio of lactide to glycolide is from about 0:100 to about 100:0, thereby providing other release rates.

Some embodiments of the microspheres or microparticles comprise hollow and/or porous interiors. In some embodiments, the microspheres comprise a solid or porous outer shell. Some embodiments of formulations comprising a porous outer shell and/or microsphere exhibits a biphasic release profile of the active ingredient(s) with an initial release burst of the active ingredient(s), followed by a sustained release associated with degradation of the polymeric microspheres. The initial burst loads the tissue with an effective lipolytic/adipogenesis inhibitory concentration of the active ingredient(s), with the subsequent slower release maintaining the desired concentration. In some embodiments, the different microsphere structures and active ingredient release profiles optimize the treatment effect of adipose tissue and adipocytes through adrenergic receptor modulation. In some preferred embodiments, sustained local tissue concentrations of long-acting selective beta-2 adrenergic agents, such as salmeterol 1 and/or formoterol 2 at concentrations of about 10 pM to about 10 µM.

In some embodiments, one or more of the active ingredients are encapsulated, bound, and/or conjugated to the polymer at a ratio of about 10-12% by mass compared to the polymer microspheres. The amount of active ingredient as a mass percentage of the carrier (e.g., microparticles or microspheres) is referred to herein as "active ingredient loading." As used herein, the terms "loaded" and "loading" refer to active ingredients substantially encapsulated bound, and/or conjugated to a carrier. In some embodiments, the active ingredient loading is up to about 75%. Thus, some preferred formulations comprise one or more beta-2 adrenergically active ingredients, such as salmeterol 1, formoterol 2, and/or their physiologically acceptable salts and solvates, loaded on polymer microspheres at about 1 mg to about 20 mg of active ingredient per about 10 to about 200 milligrams of polymer. In some embodiments, a formulation with this active ingredient loading is sufficient for providing from about 15 days to about 45 days of active ingredient release at a concentration suitable to produce lipolysis and/or adipogenesis inhibition.

In some embodiments, two or more active ingredients are loaded into the same microsphere, for example, in a liposome. Thus, some embodiments, a polymer encapsulating a glucocorticosteroid in the adrenergic compound is delivered simultaneously to the adipose tissue. Alternatively, the two active ingredients are loaded on separate microspheres. The two types of microspheres are then mixed to obtain a formulation with the desired ratio of beta-receptor agonist and glucocorticosteroid, then administered simultaneously. Alternatively, the two types of microspheres are administered sequentially.

The microspheres comprising the active ingredient(s) are suspended in from about 10 mL to 20 mL of an appropriate physiologically acceptable liquid carrier. In some embodiments using separate microspheres of the active ingredients, the microspheres are mixed together in the liquid carrier. In other embodiments, each type of microspheres is separately mixed with a liquid carrier. In some embodiments, the microsphere suspension is then injected subcutaneously just below the dermis in 1.0 mL aliquots to cover an approximate 2.0 cm$^2$ area per mL of the microsphere suspension, for example, for the treatment of cellulite. In some embodiments, from about 10 to about 20 injections are administered to cover an area of from about 20 cm$^2$ to about 40 cm$^2$. Larger and/or smaller areas are treated in other embodiments. Alternatively, bolus injections 1.0 mL to 10.0 mL are injected into fat accumulations, such as the periorbital regions, submental regions, lateral hips, and buttocks. Alternatively, injections as described above are made separately and sequentially in the same locations using two microsphere formulations encapsulating each active ingredient.

In some embodiments using needleless injection, the microparticulate formulations are injected as suspensions or as the powdered loaded microparticles, that is, without a liquid carrier.

In some embodiments, the glucocorticosteroid, such as dexamethasone 6, budesonide 8, and/or fluticasone propionate 7, also act as anti-inflammatory agents thereby reducing inflammation caused by administration of the formulation, for example, caused by polymers, polymeric microspheres, and/or liposomes in a sustained release formulation.

PLGA 15 microspheres encapsulate hydrophobic compounds more readily than hydrophilic compounds. To increase loading of hydrophilic active ingredients, in some embodiments, the microspheres are modified with polyethylene glycol units, as discussed above. Microspheres of certain sizes are substantially not absorbed into the blood or removal by lymph, thereby providing release of the active ingredient(s) in the desired location. For example, in some embodiments, the microspheres are from about 20 µm to about 200 µm in diameter. In some embodiments, the size of the microsphere also affects the release profile of the active ingredient(s) in the tissue. In genral, larger microspheres tend to provide a longer and more uniform release profile.

An exemplary sustained release formulation comprises about 0.5 milligrams to about 7.5 milligrams of salmeterol 1 and/or formoterol 2, and about 1.5 milligrams to about 7.5 milligrams of dexamethasone 6, fluticasone propionate 7, and/or budesonide 8 encapsulated in about 100 milligrams of polylactide glycolide (PLGA) 15 copolymer microspheres at a ratio of about 70 lactide:30 glycolide. In some embodiments, the copolymer ratio and active ingredient encapsulation deliver up to about 1.0 µg per day of salmeterol 1 and/or up to about 0.5 µg of formoterol, and up to 5 µg per day of fluticasone and/or budesonide 6 per about 1 mg of copolymer for up to about 30 days.

Some embodiments comprise non-sustained release formulations. In some embodiments, the duration of activity of long-acting selective beta-2 agonists in non-sustained release formulations, after a signal dose, is greater than about four hours and preferably up to about 12, or up to about 24 hours. In contrast, short-acting selective beta-2 agonists under similar conditions, have activities of less than about four hours and is less than about one hour. An exemplary non-sustained release injectable formulation comprises from about 100 µg to about 250 µg of salmeterol xinafoate and from about 500 µg to about 1000 µg of fluticasone propionate 7 formulated in up to about a 10 mL lipid-based excipient such as Cremophor® or equivalent.

In some embodiments, formulations are delivered transdermally using any suitable method known in the art, for example, as a topically applied cream or through a patch. Alternatively, other transdermal delivery means known in the art are also useful, for example, electrical. In, particular, long-acting beta-2 agonists, such as formoterol 2, salmeterol 1, or bambuterol 3, and glucocorticosteroids are suited for topical application to the skin due to their hydrophobicity. Sustained release embodiments of transdermally deliverable formulations are provided as known in the art, for example, using a biodegradable, biocompatible active ingredient-polymer formulation or liposome formulation, as discussed above.

While certain embodiments have been described, these embodiments have been presented by way of example only, and are not intended to limit the scope of the disclosure. Those skilled in the art will understand that the formulations, methods, and systems described herein may be embodied in a variety of other forms. Furthermore, various omissions, substitutions and changes in the form of the formulations, methods, and systems described herein may be made without departing from the spirit of this disclosure. The accompanying claims and their equivalents are intended to cover such forms or modifications.

What is claimed is:

1. An injectable formulation for treating regional adipose tissue or regional fat accumulation consisting essentially of:
    an effective amount of a long acting beta-2 adrenergic receptor agonist that is selected from the group consisting of salmeterol, formoterol, and salts thereof;
    an effective amount of a glucocorticosteroid that is selected from the group consisting of dexamethasone, prednisolone, fluticasone, budesonide, and salts thereof;
    a liquid carrier; and
    a pharmaceutically acceptable excipient;
    the salmeterol, formoterol, and salts thereof, the glucocorticosteroid, the liquid carrier and the pharmaceutically acceptable excipient formulated for injection into a layer of subcutaneous fat in a human in need.

2. The formulation of claim 1, wherein the formulation allows dispersal of (a) the salmeterol, formoterol, and salts thereof, and (b) the glucocorticosteroid, into the layer of subcutaneous fat at a regional fat site selected from a submental region, a waist, a hip, a lateral buttock or a thigh.

3. The formulation of claim 1, wherein salmeterol is present as a salt.

4. The formulation of claim 1, wherein the glucocorticosteroid is fluticasone propionate.

5. The formulation of claim 1, wherein the liquid carrier is a lipophilic liquid carrier.

6. A method for treating a fat accumulation comprising administering an injectable formulation of claim 1.

7. The method claim 6, wherein the pharmaceutically effective amount of salmeterol is up to about 100 µg/day.

8. The method claim 6, wherein the pharmaceutically effective amount of formoterol is up to about 50 µg/day.

9. A method for reducing adipose tissue comprising administering an injectable formulation of claim 1.

10. A method for treating regional fat accumulations or cellulite comprising
    administering to a regional fat accumulation or cellulite an injectable formulation of claim 1.

* * * * *